(12) United States Patent
Ono et al.

(10) Patent No.: US 6,710,214 B2
(45) Date of Patent: Mar. 23, 2004

(54) HIGHLY BRANCHED PERFLUOROOLEFINS, SUPER-STABLE PERFLUOROALKYL RADICALS AND PRODUCTION METHODS THEREOF

(75) Inventors: Taizo Ono, Nagoya (JP); Masakazu Nishida, Nagoya (JP); Masaharu Okazaki, Nagoya (JP); Kazumi Toriyama, Nagoya (JP); Tetsuo Shimizu, Settsu (JP)

(73) Assignees: National Institute of Advanced Industrial Science and Technology, Tokyo (JP); Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/291,699

(22) Filed: Nov. 12, 2002

(65) Prior Publication Data

US 2003/0097031 A1 May 22, 2003

(30) Foreign Application Priority Data

Nov. 16, 2001 (JP) ......................................... 2001-352474

(51) Int. Cl.$^7$ .......................... C07C 21/18; C07C 19/08; C07C 23/00

(52) U.S. Cl. ...................... 570/136; 570/124; 570/134; 570/135

(58) Field of Search ................................ 570/136, 124, 570/134, 135

(56) References Cited

U.S. PATENT DOCUMENTS 4,173,654 A * 11/1979 Scherer ........................ 424/350
4,626,608 A    12/1986 Scherer, Jr. et al.

* cited by examiner

*Primary Examiner*—Porfirio Nazario-Gonzalez
*Assistant Examiner*—Elvis O. Price
(74) *Attorney, Agent, or Firm*—Sughrue Mion, PLLC

(57) ABSTRACT

The present invention is to provide a method for producing a highly branched perfluoroolefin conveniently in a high yield, a novel highly branched perfluoroolefin, a method for producing a super-stable perfluoroalkyl radical and a novel super-stable perfluoroalkyl radical.

The present invention is a production method of a perfluoroolefin which comprises reacting a hexafluoropropene trimer with a trialkylperfluoroalkylsilane in an aprotic polar solvent using a fluoride ion as a catalyst.

2 Claims, No Drawings

HIGHLY BRANCHED PERFLUOROOLEFINS, SUPER-STABLE PERFLUOROALKYL RADICALS AND PRODUCTION METHODS THEREOF

FIELD OF THE INVENTION

The present invention relates to a highly branched perfluoroolefin, a production method of the highly branched perfluoroolefin comprising reacting a hexafluoropropene trimer with a trialkylperfluoroalkylsilane, a super-stable perfluoroalkyl radical and a method for producing a super-stable perfluoroalkyl radical by fluorinating the highly branched perfluoroolefin.

PRIOR ART

As a super-stable perfluoroalkyl radical which is highly stable, Japanese Kokoku Publication Hei-1-29175, for example, discloses perfluoro(2,4-dimethyl-3-isopropyll-3-pentyl) and the like.

In this gazette, it is described that perfluoro(2,4-dimethyl-3-isopropyl-3-pentyl) generates a free trifluoromethyl radical by, for example, heating, and this free trifluoromethyl radical can be employed, for example, as a polymerization catalyst.

A super-stable perfluoroalkyl radical is known to be obtained, for example, by fluorinating a corresponding perfluoroolefin. In this case, the perfluoroolefin acts as a precursor for the super-stable perfluoroalkyl radical.

As a method for synthesizing a perfluoroolefin, a method for oligomerizing a hexafluoropropene using an amine-based catalyst is known.

As this oligomerization method, for example, the method for producing a mixture of three kinds of hexafluoropropene trimers in the presence of tris[2(2H-hexafluoropropoxy)ethyl]amine and 1,4-diazabicyclo[2.2.2]octane using dimethyl sulfoxide as a solvent is reported (T. Martini and S. P. v. Halasz, Tetrahedron Lett., 2129–2132 (1974)).

As three kinds of hexafluoropropene trimers, there may be mentioned perfluoro(3-ethyl-2,4-dimethyl-2-pentene), perfluoro(4-methyl-3-isopropyl-2-pentene) and perfluoro(2,4-dimethyl-3-heptene).

Among those listed above, perfluoro(4-methyl-3-isopropyl-2-pentene) was reported, when being fluorinated directly, to give perfluoro(2,4-dimethyl-3-ethyl-3-pentyl) (hereinafter referred to as "super-stable perfluoroalkyl radical (dR)") which is a super-stable perfluoroalkyl radical at a yield of about 90% by weight (K. V. Scherer, T. Ono, K. Yamanouchi, R. Fernandez, P. Henderson, J. Am. Chem. Soc., 107, 718–719 (1985), U.S. Pat. No. 4,626,608).

Perfluoro(2,4-dimethyl-3-ethyl-3-pentyl) is known to be obtained also by fluorinating perfluoro(3-ethyl-2,4-dimethyl-2-pentene) directly.

It is known that perfluoro(2,4-dimethyl-3-ethyl-3-pentyl) and perfluoro(4-methyl-3-isopropyl-2-pentene) are heated and reacted together to give perfluoro(2,4-dimethyl-3-isopropyl-3-pentyl). In this reaction, perfluoro(2,4-dimethyl-3-ethyl-3-pentyl) is considered to act as a trifluoromethylating reagent.

However, perfluoro(2,4-dimethyl-3-isopropyl-3-pentyl) is obtained only in a trace amount by the synthesis method employing perfluoro(2,4-dimethyl-3-ethyl-3-pentyl), therefore this synthesis method is not practical. No other methods for synthesizing perfluoro(2,4-dimethyl-3-isopropyl-3-pentyl) has hitherto been known.

For synthesizing perfluoro(2,4-dimethyl-3-isopropyl-3-pentyl) at a high yield, it is considered to be desirable to use a precursor perfluoro(2,4-dimethyl-3-isopropyl-2-pentene).

Nevertheless, such a highly branched and sterically complicated perfluoroolefin is regarded to be very difficult to be synthesized, and no methods for synthesizing the same has hitherto been known. The synthesis should be conducted conveniently in a high yield for an industrial application.

Highly branched perfluoroolefins having many branched chains are considered to generate radicals as a result of fluorination, and the resultant radicals are very stable due to the steric hindrance, and thus are expected to be utilized as polymerization catalysts similar to perfluoro(2,4-dimethyl-3-isopropyl-3-pentyl).

SUMMARY OF THE INVENTION

In view of the above-mentioned state of the art, it is an objective of the present invention to provide a method for producing a highly branched perfluoroolefin conveniently in a high yield, a novel highly branched perfluoroolefin, a method for producing a super-stable perfluoroalkyl radical and a novel super-stable perfluoroalkyl radical.

The present invention is a highly branched perfluoroolefin represented by the following general formula (1):

$$[(CF_3)_2CF][(CF_3)_2CY]C=C(CF_3)Z \qquad (1)$$

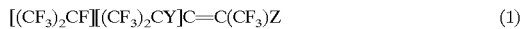

in the formula, Y and Z are the same or different and each represents F or Rf, Rf represents a straight or branched perfluoroalkyl group having 1 to 16 carbon atoms, provided that Y and Z are not simultaneously F.

The present invention is a production method of a perfluoroolefin for producing the above highly branched perfluoroolefin which comprises reacting a hexafluoropropene trimer with a trialkylperfluoroalkylsilane represented by the following general formula (2):

$$(2)$$

$$R^2 \!-\! \underset{\underset{R^3}{|}}{\overset{\overset{R^1}{|}}{Si}} \!-\! Rf$$

in the formula, Rf represents a straight or branched perfluoroalkyl group having 1 to 16 carbon atoms, $R^1$, $R^2$ and $R^3$ are the same or different and each represents an alkyl group having 1 to 3 carbon atoms, in an aprotic polar solvent using a fluoride ion as a catalyst.

The present invention is a production method of a super-stable perfluoroalkyl radical which comprises producing a super-stable perfluoroalkyl radical represented by the following general formula (1R):

$$[(CF_3)_2CF][(CF_3)_2CY]Ra\!-\!CF(CF_3)Z \qquad (1R)$$

in the formula, Ra represents a carbon atom having one unpaired electron, Y and Z are the same or different and each represents F or Rf, and Rf represents a straight or branched perfluoroalkyl group having 1 to 16 carbon atoms, provided that Y and Z are not simultaneously F,
by fluorinating the above highly branched perfluoroolefin.

The present invention is a production method of a reduced-carbon super-stable perfluoroalkyl radical which comprises producing a super-stable perfluoroalkyl radical (AR) represented by the following general formula (3R):

$$[(CF_3)_2CF]_2Ra\!-\!CF(CF_3)Rf \qquad (3R)$$

in the formula, Ra represents a carbon atom having one unpaired electron and Rf represents a straight or branched perfluoroalkyl group having 1 to 16 carbon atoms, by fluorinating a highly branched perfluoroolefin (B) represented by the following general formula (4):

$$[(CF_3)_2CF][(CF_3)_2CRf]C=C(CF_3)Rf \qquad (4)$$

in the formula, each Rf is the same or different from each other and is defined as described above.

The present invention is a super-stable perfluoroalkyl radical (BR) represented by the following general formula (4R):

$$[(CF_3)_2CF][(CF_3)_2CRf]Ra-CF(CF_3)Rf \qquad (4R)$$

in the formula, Ra represents a carbon atom having one unpaired electron and each Rf is the same or different from each other and represents a straight or branched perfluoroalkyl group having 1 to 16 carbon atoms.

The present invention is a super-stable perfluoroalkyl radical (CR) represented by the following general formula (5R):

$$[(CF_3)_2CF][(CF3)_2CRf]Ra-CF_2(CF_3) \qquad (5R)$$

in the formula, Ra represents a carbon atom having one unpaired electron and Rf represents a straight or branched perfluoroalkyl group having 1 to 16 carbon atoms.

DETAILED DISCLOSURE OF THE INVENTION

In the following, the present invention is described in detail.

The highly branched perfluoroolefin of the invention is represented by the above general formula (1).

Accordingly, the highly branched perfluoroolefin of the invention is a highly branched perfluoroolefin (A) represented by the following general formula (3):

$$[(CF_3)_2CF]_2C=C(CF_3)Rf \qquad (3)$$

in the formula, Rf represents a straight or branched perfluoroalkyl group having 1 to 16 carbon atoms, a highly branched perfluoroolefin (B) represented by the following general formula (4):

$$[(CF_3)_2CF][(CF_3)_2CRf]C=C(CF_3)Rf \qquad (4)$$

in the formula, each Rf is the same to or different from each other and represents a straight or branched perfluoroalkyl group having 1 to 16 carbon atoms, or, a highly branched perfluoroolefin (C) represented by the following general formula (5):

$$[(CF_3)_2CF][(CF_3)_2CRf]C=CF(CF_3) \qquad (5)$$

in the formula, Rf represents a straight or branched perfluoroalkyl group having 1 to 16 carbon atoms.

While the above Rf is not particularly limited provided that it is a perfluoroalkyl group having 1 to 16 carbon atoms and may be straight or branched, it is preferably a perfluoroalkyl group having 1 to 3 carbon atoms since these are easily purified and analyzed, with trifluoromethyl group being more preferred.

In the above general formula (1), Y is preferably Rf. In such case, the highly branched perfluoroolefin of the invention is the above highly branched perfluoroolefin (B) or the above highly branched perfluoroolefin (C). While the above highly branched perfluoroolefin (C) may be any of two kinds of geometric isomers, Z form is more preferred than E form because of a less steric hindrance and a sufficient stability.

The above highly branched perfluoroolefin (A) is preferably perfluoro(2,4-dimethyl-3-isopropyl-2-pentene) (hereinafter referred to as "highly branched perfluoroolefin (a)"). The above highly branched perfluoroolefin (B) is preferably perfluoro(2,4,4-trimethyl-3-isopropyl-2-pentene) (hereinafter referred to as "highly branched perfluoroolefin (b)"). The above highly branched perfluoroolefin (C) is preferably perfluoro(4,4-dimethyl-3-isopropyl-2-pentene) (hereinafter referred to as "highly branched perfluoroolefin (c)").

The highly branched perfluoroolefin of the invention is utilized not only as an intermediate for synthesizing surfactants, pharmaceuticals and pesticides, but also as a precursor for a super-stable perfluoroalkyl radical in the production method of the super-stable perfluoroalkyl radical of the invention described below.

The production method of the perfluoroolefin of the invention is a method for producing the above highly branched perfluoroolefin, and comprises reacting a hexafluoropropene trimer with a trialkylperfluoroalkylsilane represented by the above general formula (2) in an aprotic polar solvent using a fluoride ion as a catalyst.

The above hexafluoropropene trimer may for example be perfluoro(2,4-dimethyl-3-ethyl-2-pentene) (hereinafter referred to as "trimer A"), perfluoro(4-methyl-3-isopropyl-2-pentene) (hereinafter referred to as "trimer B") and perfluoro(2,4-dimethyl-3-heptene) (hereinafter referred to as "trimer C"). Among those listed above, the above trimer A and the above trimer B are preferred since the yield is preferable.

As the above hexafluoropropene trimer, one or two or more species can be used, thus, for example, only the above trimer A, only the above trimer B, a combination of the above trimer A and the above trimer B, or the mixture of these with the above trimer C may be employed. When the above trimer C is mixed, the above trimer C is preferably employed in a small amount for the purpose of raising the purity in the reaction solution.

While the above trialkylperfluoroalkylsilane is not particularly limited provided that it is represented by the above general formula (2), Rf in the above general formula (2) is preferably a straight or branched perfluoroalkyl group having 1 to 3 carbon atoms, with a trifluoromethyl group being more preferred.

In the production method of the perfluoroolefin of the invention, Rf in the above general formula (2) serves as a perfluoroalkyl group to be introduced into the above hexafluoropropene trimer. Thus, Rf in the above general formula (1) in the resultant highly branched perfluoroolefin is derived from Rf in the above general formula (2) of the above trialkylperfluoroalkylsilane molecule.

$R^1$, $R^2$ or $R^3$ in the above general formula (2) is preferably a methyl group. $R^1$, $R^2$ and $R^3$ are preferably the same to one another, and it is more preferable that all are methyl groups.

The trialkylperfluoroalkylsilane described above is preferably trifluoromethyltrimethylsilane in view of the cost of the raw material.

The aprotic polar solvent employed in the production method of the perfluoroolefin of the invention is not particularly limited, and may for example be a Glyme-based solvent, dimethyl sulfoxide (DMSO), dimethyl acetamide (DMA), dimethyl formamide (DMF), 1-methyl-2-pyrrolidone (NMP), and 1,3-dimethyl-2-imidazolidinone (DMI) and the like. The Glyme-based solvent mentioned above may for example be diethylene glycol dimethyl ether, triethylene glycol dimethyl ether, tetraethylene glycol dimethyl ether, triethylene glycol diethyl ether, tetraethylene glycol diethyl ether and the like, as well as higher homologues thereof.

The above aprotic polar solvent is preferably dimethyl formamide (DMF), 1-methyl-2-pyrrolidone (NMP) and 1,3-dimethyl-2-imidazolidinone (DMI) because of generally higher reaction rates, with 1,3-dimethyl-2-imidazolidinone (DMI) being more preferred because of higher reaction rate and higher selectivity.

The production method of the perfluoroolefin of the invention uses a fluoride ion as a catalyst. The above fluoride ion is enabled to act as a catalyst by using a compound which generates the fluoride ion.

Such a compound is not particularly limited provided that it can generate a fluoride ion, and may for example be sodium fluoride, potassium fluoride, acidic potassium fluoride, cesium fluoride, tetrabutylammonium fluoride, tetramethylammonium fluoride, tris(dimethylamino)sulfonium trimethylsilyl difluoride, tetrabutylammonium difluorotriphenyl stannate, pyridinium (hydrogen polyfluoride), triethylamine (hydrogen trifluoride) and the like. Among those listed above, pyridinium (hydrogen polyfluoride) is referred to also as Olah reagent.

While the highly branched perfluoroolefin obtained by the production method of the perfluoroolefin of the invention is not particularly limited provided that it is represented by the above general formula (1), it is preferably the above highly branched perfluoroolefin (A), more preferably the above highly branched perfluoroolefin (a). The above highly branched perfluoroolefin may preferably be the above highly branched perfluoroolefin (b) and the above highly branched perfluoroolefin (c).

The above highly branched perfluoroolefin is generally obtained as a mixture of at least two species selected from the group consisting of the above highly branched perfluoroolefin (A), the above highly branched perfluoroolefin (B) and the above highly branched perfluoroolefin (C), although it may vary depending on the species and the amount of addition of the hexafluoropropene trimer and the aprotic polar solvent as well as the reaction conditions. The following scheme shows the example in case that Rf is a trifluoromethyl group.

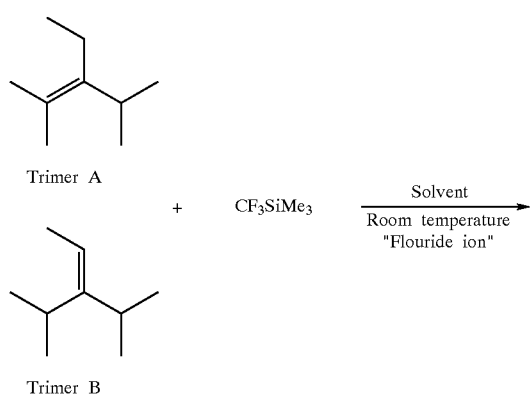

-continued
Highly branched perfluoroolefin

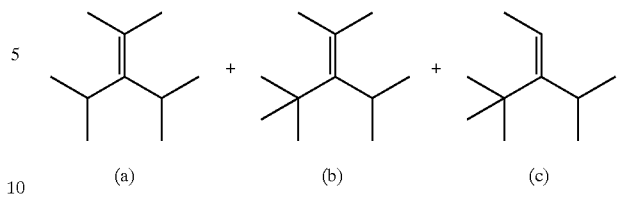

As the above highly branched perfluoroolefin, when the trimer A is employed as a hexafluoropropene trimer, the tendency is such that an yield of the highly branched perfluoroolefin (B) is high, for example 15 to 80% by weight, an yield of the highly branched perfluoroolefin (C) is significantly lower than the yield of the highly branched perfluoroolefin (B), for example 10 to 50% by weight, and an yield of the highly branched perfluoroolefin (A) is 5% by weight or less and may substantially be zero in some cases.

As the above highly branched perfluoroolefin, when the trimer B is employed as a hexafluoropropene trimer, the tendency is such that an yield of the highly branched perfluoroolefin (A) is high, for example 30 to 95% by weight, an yield of the highly branched perfluoroolefin (B) is significantly lower than the yield of the highly branched perfluoroolefin (A), for example 45% by weight or less, and an yield of the highly branched perfluoroolefin (C) is 5% by weight or less and may substantially be zero in some cases.

For the purpose of obtaining the highly branched perfluoroolefin (A) selectively in the production method of the perfluoroolefin of the invention, 1,3-dimethyl-2-imidazolidinone is preferably employed as the aprotic polar solvent. By using 1,3-dimethyl-2-imidazolidinone as the aprotic polar solvent, by-products, which are generally produced, are not produced substantially. The above highly branched perfluoroolefin (A) is preferably employed since the selectivity is high when the highly branched perfluoroolefin (a) is to be obtained.

The term "selectively" employed in this specification describing the reaction for obtaining the above highly branched perfluoroolefin (A) selectively means that the intended product is obtained in a high yield. The above term "high yield" means a yield of 60% by weight or higher.

The reaction for obtaining the above highly branched perfluoroolefin (A) selectively may be one where the starting material hexafluoropropene trimer is remained unreacted, and the amount of the unreacted material is usually 25% by weight or less of the starting material. For the purpose of obtaining the reaction product of the above highly branched perfluoroolefin (A) at a purity as high as possible, the amount of the unreacted material may be reduced, in some cases, by increasing the amount of addition of the trialkylperfluoroalkylsilane.

In the production method of the perfluoroolefin of the invention, the lower and upper limits of the reaction temperature are generally 0° C. and 70° C., respectively, and the upper limit is preferably 30° C., and the reaction may generally be conducted at room temperature without any particular need of heating, thus the method can be employed easily and enables an energy-saving operation.

The production method of the super-stable perfluoroalkyl radical of the invention comprises producing the super-stable perfluoroalkyl radical represented by the above general formula (1R) by fluorinating the above highly branched perfluoroolefin.

Such a highly branched perfluoroolefin may be any of the highly branched perfluoroolefins of the invention listed above, and these can be obtained by the production method of the perfluoroolefin of the invention as described above.

The highly branched perfluoroolefin employed in the production method of the super-stable perfluoroalkyl radical of the invention is preferably the highly branched perfluoroolefin (a), highly branched perfluoroolefin (b) or highly branched perfluoroolefin (c) described above, with the highly branched perfluoroolefin (a) being more preferred since the super-stable perfluoroalkyl radical can be synthesized in a high yield. While two or more species may be employed as the above highly branched perfluoroolefins, it is preferable to use one species for the purpose of increasing the purity of the resultant super-stable perfluoroalkyl radical.

The fluorination in the production method of the super-stable perfluoroalkyl radical of the invention is preferably conducted using a fluorine gas. The above fluorine gas may be a diluted one or a neat one without dilution. The dilution of the above fluorine gas may be conducted with an inert gas such as nitrogen or argon. The fluorine gas described above is preferably a pure one.

The fluorination in the production method of the super-stable perfluoroalkyl radical of the invention can generally be conducted by introducing a diluted fluorine gas or neat pure fluorine gas into the bottom of the reaction vessel, or also by effecting the reaction under pressure with a fluorine gas in the sealed vessel. The pressure of the fluorine gas may be 10 atoms (absolute pressure), preferably 1 to 10 atoms (absolute pressure).

Such a fluorination results in the addition of a fluorine atom to one of the double bond-forming carbon atoms of the highly branched perfluoroolefin, whereby obtaining a super-stable perfluoroalkyl radical having an unpaired electron on the other carbon atom of said double bond-forming carbon atoms. In this specification, the above fluorination may be referred to as a "direct fluorination".

During the fluorination described above, when it is conducted under the condition of 1 atom (absolute pressure), the reaction temperature is preferably 40° C. or lower, more preferably 30° C. or lower, for the purpose of raising the yield of the super-stable perfluoroalkyl radical; preferably −10° C. or higher, more preferably 0° C. or higher, for the purpose of promoting the reaction; and when the yield and the promotion of the reaction are taken into account, the upper limit is preferably 10° C., more preferably 5° C., and the lower limit is preferably −10° C., more preferably −5° C.

During the fluorination described above, when it is conducted under the condition of 1 atom (absolute pressure), the aeration time period is generally preferably 500 hours or longer, more preferably 720 hours or longer, for the purpose of raising the yield of the super-stable perfluoroalkyl radical.

The fluorination described above is conducted preferably under pressure and/or at a low temperature such as −5 to 5° C., for instance, for the purpose of reducing the reaction time, preferably under pressure and at a low temperature such as −5 to 5° C. especially for the purpose of industrial application.

The super-stable perfluoroalkyl radical to be obtained by the production method of the super-stable perfluoroalkyl radical of the invention is not particularly limited provided that it is represented by the above general formula (1R).

While Rf in the above general formula (1R) is not particularly limited provided that it is a perfluoroalkyl group having 1 to 16 carbon atoms and may be straight or branched, it is preferably a perfluoroalkyl group having 1 to 3 carbon atoms since it is easily purified and analyzed, with a trifluoromethyl group being more preferred. The above Rf is derived from Rf in the above general formula (1) representing the highly branched perfluoroolefin employed in the production method of the super-stable perfluoroalkyl radical of the invention.

In the above general formula (1R), Ra is a carbon atom having one unpaired electron. The term "carbon atom having one unpaired electron" employed herein means a carbon having, on the atom, an unpaired electron possessed by a free radical.

The super-stable perfluoroalkyl radical represented by the above general formula (1R) is a super-stable perfluoroalkyl radical (AR) represented by the following general formula (3R):

$$[(CF_3)_2CF]_2Ra\text{—}CF(CF_3)Rf \qquad (3R)$$

in the formula, Ra represents a carbon atom having one unpaired electron and Rf represents a straight or branched perfluoroalkyl group having 1 to 16 carbon atoms, a super-stable perfluoroalkyl radical (BR) represented by the following general formula (4R):

$$[(CF_3)_2CF][(CF_3)_2CRf]Ra\text{—}CF(CF_3)Rf \qquad (4R)$$

in the formula, Ra represents a carbon atom having one unpaired electron and each Rf is the same or different from each other and represents a straight or branched perfluoroalkyl group having 1 to 16 carbon atoms, or, a super-stable perfluoroalkyl radical (CR) represented by the following general formula (5R):

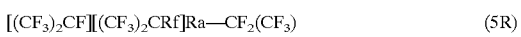

$$[(CF_3)_2CF][(CF_3)_2CRf]Ra\text{—}CF_2(CF_3) \qquad (5R)$$

in the formula, Ra represents a carbon atom having one unpaired electron and Rf represents a straight or branched perfluoroalkyl group having 1 to 16 carbon atoms.

The above super-stable perfluoroalkyl radical (AR) is preferably perfluoro(2,4-dimethyl-3-isopropyl-3-pentyl) (hereinafter referred to as "super-stable perfluoroalkyl radical (aR)"). The above super-stable perfluoroalkyl radical (BR) is preferably perfluoro(2,4,4-trimethyl-3-isopropyl-3-pentyl) (hereinafter referred to as "super-stable perfluoroalkyl radical (bR)"). The above super-stable perfluoroalkyl radical (CR) is preferably perfluoro(4,4-dimethyl-3-isopropyl-3-pentyl) (hereinafter referred to as "super-stable perfluoroalkyl radical (cR)").

As a super-stable perfluoroalkyl radical to be obtained by the production method of the super-stable perfluoroalkyl radical of the invention, the above super-stable perfluoroalkyl radical (AR) is obtained as a main product from the above highly branched perfluoroolefin (A), the above super-stable perfluoroalkyl radical (BR) is obtained as a main product from the above highly branched perfluoroolefin (B), and the above super-stable perfluoroalkyl radical (CR) is obtained as a main product from the above highly branched perfluoroolefin (C), depending on the species of the highly branched perfluoroolefin employed and the reaction conditions.

Accordingly, as shown in the following scheme, as the main product by the production method of the super-stable perfluoroalkyl radical of the invention, the above super-stable perfluoroalkyl radical (aR) is obtained from the above highly branched perfluoroolefin (a), the above super-stable perfluoroalkyl radical (bR) is obtained from the above highly branched perfluoroolefin (b) and the above super-stable perfluoroalkyl radical (cR) is obtained from the above highly branched perfluoroolefin (c).

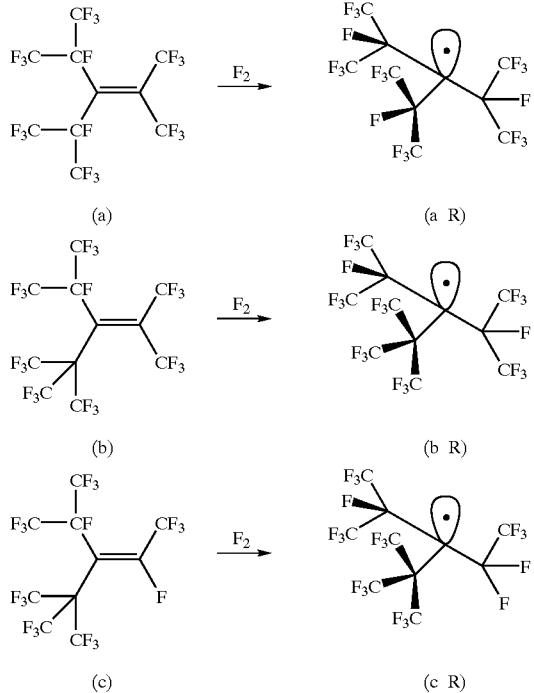

The above super-stable perfluoroalkyl radical is, usually, sufficiently stable at a temperature below 90° C., depending on the chemical structure, however. While the above super-stable perfluoroalkyl radical is decomposed by heating, for example, to undergo β-cleavage to generate a free trifluoromethyl radical, it usually has a half life of 6 hours or longer at a temperature below 90° C.

Especially, the above super-stable perfluoroalkyl radical (aR) is highly stable such that it does not react even with a pure fluorine gas at 0° C., and undergoes no chemical change at room temperature over a period longer than one year. The above super-stable perfluoroalkyl radical (aR) is decomposed at a half-life of about 6 hours when heated at 90° C. to generate a free trifluoromethyl radical.

Since the super-stable perfluoroalkyl radical is extremely and sufficiently stable as discussed above, a perfluoroalkyl radical with low molecular weight such as trifluoromethyl released upon heating at, for example, 90° C. or higher can be employed not only as an initiator in a polymer synthesis, but also as a standard substance for electron spin resonance (ESR), surface treatment reagent, leak checking reagent for a container with a complicated shape, emulsion as a contrast agent for biological imaging.

Among them, the above super-stable perfluoroalkyl radical (aR) and the above super-stable perfluoroalkyl radical (bR), especially the above super-stable perfluoroalkyl radical (aR), can be employed preferably as standard substrates for ESR, since they are highly symmetric.

The production method of the reduced-carbon super-stable perfluoroalkyl radical of the invention comprises producing the super-stable perfluoroalkyl radical (AR) by fluorinating the highly branched perfluoroolefin (B).

The above highly branched perfluoroolefin (B) and the above super-stable perfluoroalkyl radical (AR) are similar to those described above, and the fluorination mentioned above is conducted by the method similar to the fluorination as described above with regard to the production method of the super-stable perfluoroalkyl radical of the invention.

The production method of the reduced-carbon super-stable perfluoroalkyl radical of the invention comprises fluorinating the above highly branched perfluoroolefin (B) to produce the above super-stable perfluoroalkyl radical (AR) having a number of carbon atom lower than that of the above highly branched perfluoroolefin (B).

While the reaction temperature of the production method of the reduced-carbon super-stable perfluoroalkyl radical of the invention is not particularly limited, the preferable lower limit and upper limit are −78° C. and 45° C., more preferably −10° C. and 15° C., respectively.

The mechanism of this reaction has not been elucidated clearly, but it is considered such that, by the above fluorination, a fluorine atom is added to a double bond to form an unpaired electron and then the unpaired electron dissociates one Rf in the general formula (4) representing the above highly branched perfluoroolefin (B) to release as a free radical. This reaction tends to occur easily especially when the fluorination is carried out using a pure fluorine gas at a reaction temperature of 0° C. to room temperature. The above Rf is preferably a trifluoromethyl group.

In the production method of the super-stable perfluoroalkyl radical of the invention, the above super-stable perfluoroalkyl radical (AR), as described above, can be obtained from the highly branched perfluoroolefin (A) whose number of carbon atom is the same as that of the above super-stable perfluoroalkyl radical (AR). This reaction is proceeded quantitatively when performing the fluorination using a pure fluorine gas at a reaction temperature especially about 0° C.

Therefore, by adjusting the reaction temperature, the intended super-stable perfluoroalkyl radical can be obtained. Such an adjustment of the reaction temperature is considered to be useful especially when the highly branched perfluoroolefin employed is a mixture comprising the above highly branched perfluoroolefin (A) and the above highly branched perfluoroolefin (B).

As the example of the reaction for obtaining the above super-stable perfluoroalkyl radical (AR) by the production method of the reduced-carbon super-stable perfluoroalkyl radical of the invention and the reaction for obtaining the same by the above production method of the super-stable perfluoroalkyl radical, reactions for obtaining the super-stable perfluoroalkyl radical (aR) from a highly branched perfluoroolefin (b) and from a highly branched perfluoroolefin (a) are described in the following scheme.

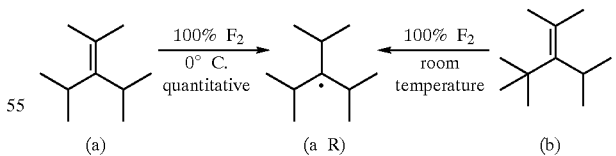

The reaction for formation of the super-stable perfluoroalkyl radical (AR) by the production method of the reduced-carbon super-stable perfluoroalkyl radical of the invention may be accompanied with the reaction for formation of the super-stable perfluoroalkyl radical (BR) by the production method of the super-stable perfluoroalkyl radical described above, simultaneously.

The highly branched perfluoroolefin of the invention, which has a chemical structure described above, is a novel compound and can be used as a precursor for the super-stable perfluoroalkyl radical as described above.

The production method of the perfluoroolefin of the invention allows the above highly branched perfluoroolefin to be obtained in a high yield by a convenient method as described above.

Since the production method of the super-stable perfluoroalkyl radical of the invention allows the super-stable perfluoroalkyl radical to be obtained in a high yield with high purity by an inexpensive and convenient method and the reaction scale can be enlarged easily, it is suitable to an industrial application which requires a large scale synthesis.

The production method of the reduced-carbon super-stable perfluoroalkyl radical of the invention allows the super-stable perfluoroalkyl radical (AR) to be obtained in a high yield by a convenient method and can give a wider option in selecting the method for producing the above highly stable perfluoroalkyl radical (AR).

The above-mentioned super-stable perfluoroalkyl radical (BR) is also encompassed within the present invention. As the above super-stable perfluoroalkyl radical (BR), the super-stable perfluoroalkyl radical (bR) described above is preferred.

The super-stable perfluoroalkyl radical (CR) described above is also encompassed within the present invention. As the above super-stable perfluoroalkyl radical (CR), the super-stable perfluoroalkyl radical (cR) described above is preferred.

Since the above super-stable perfluoroalkyl radical (BR) and the super-stable perfluoroalkyl radical (CR) are sufficiently stable, as described above, each of them is heated to 90° C. or higher to liberate a perfluoroalkyl radical having a low molecular weight such as trifluoromethyl, whereby being utilized as a polymerization initiator.

The production method of the perfluoroolefin of the invention allows the highly branched perfluoroolefin to be obtained by a convenient method in a high yield. The production method of the super-stable perfluoroalkyl radical of the invention enables a simple and efficient production of the super-stable perfluoroalkyl radical which was obtained only in a small amount by conventional methods. The super-stable perfluoroalkyl radical of the invention is sufficiently stable, and its ability of generating a radical upon heating makes it applicable to various applications. The highly branched perfluoroolefin of the invention can be a precursor for the above super-stable perfluoroalkyl radical.

EXAMPLES

The following examples illustrate the present invention in further detail. These examples are, however, by no means limitative of the scope of the present invention. $^{19}$F-NMR (282.24 MHz) described in examples were measured using deuterated chloroform as a solvent and fluoroform ($CFCl_3$) as an internal standard. Each chemical shift value in $^{19}$F-NMR was represented as δ ppm with an absorption at a magnetic field higher than fluoroform being regarded as negative. For gas chromatography measurement, a capillary column (NB-1, 0.25 μm, 1.5 mm ID×60 m) was used and an FID was used as a detector. For preparative gas chromatography, a packed column whose mobile phase was Fomblin was used. Mass spectroscopy (MS) was measured using a gas chromatograph-quadrupole mass spectrometer (GC-MS), with the ionization voltage of 70 eV. Paramagnetic nuclear magnetic resonance absorption spectrum (ESR) was measured using FC-72 (perfluorocarbon containing perfluorohexane as a main component) as a solvent.

Example 1

Synthesis of Perfluoro(2,4-dimethyl-3-isopropyl-2-pentene)

1 mmol (450 mg) of a hexafluoropropene trimer mixture (containing 10% by weight of perfluoro(3-ethyl-2,4-dimethyl-2-pentene)) whose main component was perfluoro(4-methyl-3-isopropyl-2-pentene) and 1.1 mmol (23.4 mg) of trifluoromethyltrimethylsilane were weighed into a 10-ml fluororesin-made reaction container, and 1 ml of dimethyl formamide and 0.3 mmol of acidic potassium fluoride ($KHF_2$) were added. A fluororesin-made magnetic stirrer was placed therein, and the mixture was stirred vigorously for 1 hour at room temperature. The transparent lower perfluorocarbon layer was separated into each component by preparative gas chromatography (using a column whose mobile phase was Fomblin), and the structure was identified by $^{19}$F-NMR. The yield of a main product perfluoro(2,4-dimethyl-3-isopropyl-2-pentene) calculated on the basis of the ratio of the peak areas in the gas chromatography using a capillary column (NB-1, 0.25 μm, 1.5 mm ID×60 m) was 62.7% by weight.

$^{19}$F-NMR: 56.07 (3F, doublet quartet, J=58.6, 12.0 Hz), 59.35(3F,septet quartet, J=15.5, 12.0 Hz), 70.11(6F, multiplet), 70.56(6F,broad doublet, J=36.4 Hz), 153.6(1F, septet doublet, J=35.7, 12.7 Hz), 157.5(1F,quartet doublet, J=58.6, 12.0 Hz)

MS(m/z,%): 481(M-F,1.3), 393($C_9F_{15}$,1.9), 343 ($C_8F_{13}$, 2.2), 293($C_7F_{11}$,2.5), 243($C_6F_9$,1.7), 205($C_5F_4CF_3$,1.7), 181 (C155($C_5F_5$,1.7), 124($C_4F_4$,1.0), 119($C_2F_5$,1.3), 100($C_2F_4$, 1.3), 93($C_3F_3$,1.3), 69($CF_3$,100)

As the by-products, perfluoro(4,4-dimethyl-3-isopropyl-2-pentene) and perfluoro(2,4,4-trimethyl-3-isopropyl-2-pentene) were obtained at the yields of 2.6% by weight and 13.3% by weight, respectively. Starting materials perfluoro(4-methyl-3-isopropyl-2-pentene) and perfluoro(3-ethyl-2,4-dimethyl-2-pentene) were contained at the levels of 7.1% by weight and 14.2% by weight, respectively.

$^{19}$F-NMR of perfluoro(4,4-dimethyl-3-isopropyl-2-pentene): 60.05(9F,doublet quartet,J=26.7,13.2 Hz), 66.29 (3F,decaplet doublet,J=11.7,4.3 Hz), 67.03(1F,septet doublet quartet,39.7,15.5,4.2 Hz), 72.38 (6F,doublet,J=39.5 Hz), 166.3(1F,decaplet doublet, J=26.7,15.5 Hz).

MS (m/z,%) of perfluoro(4,4-dimethyl-3-isopropyl-2-pentene): 393($C_9F_{15}$, 3.6), 343($C_8F_{13}$, 2.1), 293($C_7F_{11}$, 1.7), 255($C_5F_3(CF_3)_2$,0.7), 243($C_6F_9$, 1.4), 205($C_5F_4CF_3$,1.2), 200($C_4F_8$,0.9), 181($C_4F_7$,1.0), 155(C5$F_5$,1.0), 150($C_3F_6$, 0.6), 143($C_4F_5$,1.3), 131($C_3F_5$,1.1), 124($C_4F_4$,1.2), 119 ($C_2F_5$,2.3), 117($C_5F_3$, 0.7), 100($C_2F_4$,1.1), 93($C_3F_3$,1.8), 69($CF_3$,100), 50($CF_2$,0.8)

$^{19}$F-NMR of perfluoro(2,4,4-trimethyl-3-isopropyl-2-pentene): 55.09(3F,septet,J=12.9 Hz), 56.83(3F,decaplet,J= 15.5 Hz), 57.98(9F,broad singlet), 70.40(6F,broad singlet), 146.99(1F,decaplet,J=31.7 Hz) MS(m/z,%) of perfluoro(2, 4,4-trimethyl-3-isopropyl-2-pentene): 443($C_{10}F_{17}$,1.1), 393 ($C_9F_{15}$,0.9), 355($C_5F_2(CF_3)_2(C_2F_5)$,0.7), 293($C_7F_{11}$,1.0), 243($C_6F_9$,0.6), 205($C_5F_4CF_3$,1.7), 200($C_4F_8$,0.7), 181 ($C_4F_7$,1.8), 155($C_5F_5$,1.0), 131($C_3F_5$,0.9), 124($C_4F_4$,0.7), 117($C_5F_3$,0.7), 100($C_2F_4$,0.7), 93($C_3F_3$,1.1), 69($CF_3$,100), 50($CF_2$,0.7).

Example 2

Synthesis of Perfluoro(2,4-dimethyl-3-isopropyl-2-pentene)

1 mmol (450 mg) of a hexafluoropropene trimer mixture (containing 10% by weight of perfluoro(3-ethyl-2,4-dimethyl-2-pentene)) whose main component was perfluoro(4-methyl-3-isopropyl-2-pentene) and 4.0 mmol (568.8 mg) of trifluoromethyltrimethylsilane were weighed into a 10-ml fluororesin-made reaction container, and 1 ml of dimethyl formamide and 0.1 mmol of acidic potassium fluoride (KHF$_2$, 7.8 mg) were added. A fluororesin-made magnetic stirrer was placed therein, and the mixture was stirred vigorously for 1 hour at room temperature. The transparent lower perfluorocarbon layer was analyzed by gas chromatography using a capillary column (NB-1, 0.25 µm, 1.5 mm ID×60 m). The yields of the main product perfluoro(2,4-dimethyl-3-isopropyl-2-pentene) and perfluoro(2,4,4-trimethyl-3-isopropyl-2-pentene) were 63.5% by weight and 36.5% by weight, respectively.

Accordingly, it was revealed that the reaction conditions described above allowed only the by-product perfluoro(2,4,4-trimethyl-3-isopropyl-2-pentene) to be contained but did not allow perfluoro(4,4-dimethyl-3-isopropyl-2-pentene) to be contained.

Example 3

Selective synthesis of perfluoro(2,4-dimethyl-3-isopropyl-2-pentene)

1 mmol (450 mg) of a hexafluoropropene trimer mixture (containing 10% by weight of perfluoro(3-ethyl-2,4-dimethyl-2-pentene)) whose main component was perfluoro (4-methyl-3-isopropyl-2-pentene) and 2.0 mmol (284.4 mg) of trifluoromethyltrimethylsilane were weighed into a 10-ml fluororesin-made reaction container, then 1 ml of 1,3-dimethyl-2-imidazolidinone and 0.1 mmol of acidic potassium fluoride (KHF$_2$, 7.8 mg) were added therein. A fluororesin-made magnetic stirrer was placed and the mixture was stirred vigorously for 1 hour at room temperature, and then 1.0 mmol of trifluoromethyltrimethylsilane (142.2 mg) and 0.1 mmol of acidic potassium fluoride (KHF$_2$, 7.8 mg) were added and the mixture was further stirred vigorously for 1 hour at room temperature. After completion of the reaction, the transparent lower perfluorocarbon layer was analyzed by gas chromatography using a capillary column (NB-1, 0.25 µm, 1.5 mm ID×60 m). The yield of the main product perfluoro(2,4-dimethyl-3-isopropyl-2-pentene) was 89.6% by weight. The remainders were the starting materials perfluoro(4-methyl-3-isopropyl-2-pentene) and perfluoro(3-ethyl-2,4-dimethyl-2-pentene), which were present at 4.2% by weight and 2.6% by weight, respectively.

Example 4

Synthesis of Perfluoro(2,4,4-trimethyl-3-isopropyl-2-pentene)

1 mmol (450 mg) of perfluoro(3-ethyl-2,4-dimethyl-2-pentene) and 4.0 mmol (568.8 mg) of trifluoromethyltrimethylsilane were weighed into a 10-ml fluororesin-made reaction container, then 1 ml of dimethyl formamide and 0.1 mmol of acidic potassium fluoride (KHF$_2$, 7.8 mg) were added therein. A fluororesin-made magnetic stirrer was placed and the mixture was stirred vigorously for 1 hour at room temperature, and then 1.0 mmol of trifluoromethyltrimethylsilane (142.2 mg) and 0.1 mmol of acidic potassium fluoride (KHF$_2$, 7.8 mg) were added and the mixture was further stirred vigorously for 1 hour at room temperature. After completion of the reaction, the transparent lower perfluorocarbon layer was analyzed by gas chromatography using a capillary column (NB-1, 0.25 µm, 1.5 mm ID×60 m). The yield of the main product perfluoro(2,4,4-trimethyl-3-isopropyl-2-pentene) was 74.5% by weight. As the by-product, perfluoro 4,4-dimethyl-3-isopropyl-2-pentene was obtained at the yield of 25.5% by weight. The starting material perfluoro(3-ethyl-2,4-dimethyl-2-pentene) was consumed completely by the reaction.

Example 5

Direct Fluorination of Perfluoro(2,4-dimethyl-3-isopropyl-2-pentene) (Room Temperature)

A 20-ml Hauk cylinder was charged with perfluoro(2,4-dimethyl-3-isopropyl-2-pentene) (12 g, 24 mmol) obtained in Example 3, then a fluororesin-made magnetic stirrer was placed therein and connected with the fluorine line. The cylinder was cooled with liquid nitrogen, and the inside pressure was reduced by a vacuum pump. After three freeze-and-thaw cycles followed by purging the container with nitrogen, a pure fluorine gas was introduced via the line, and the reaction was conducted at room temperature under the condition of 1 atom (absolute pressure) with stirring. After reaction for 10 days, the reaction solution was taken out and analyzed by gas chromatograph-quadrupole mass spectrometer (GC-MS) and ESR. The yield of perfluoro(2,4-dimethyl-3-isopropyl-3-pentyl) on the basis of the ratio of the peak areas in the gas chromatography was 51% by weight. The remainder 49% by weight corresponded to the saturated form of perfluoro(2,4-dimethyl-3-isopropylpentane). Perfluoro(2,4-dimethyl-3-isopropyl-3-pentyl) was fractionated and purified by gas chromatography using a packed column whose mobile phase was Fomblin, and dissolved in FC-72 (perfluoroalkane containing perfluorohexane as a main component) to prepare an ESR sample. The structure was identified by MS and ESR.

MSm/z(%): 481($C_{10}F_{19}$,0.3), 431($C_9F_{17}$,0.6), 393($C_9F_{15}$, 0.6), 381($C_8F_{15}$,0.6), 362($C_8F_{14}$,1.2), 355($C_9F_{13}$,1.3), 343 ($C_8F_{13}$,2.8), 293($C_7F_{11}$,3.7), 281($C_6F_{11}$,5.9), 267($C_8F_9$,1.4), 255($C_7F_9$,0.3), 243($C_6F_9$,2.2), 231($C_5F_9$,0.2), 205($C_6F_7$, 1.0), 193($C_5F_7$,1.2), 181($C_4F_7$,0.8), 169($C_3F_7$,0.3), 155 ($C_5F_5$,1.0), 150($C_3F_6$,1.3), 143($C_4F_5$,1.2), 131($C_3F_5$,0.8), 124($C_4F_4$,1.1), 119($C_2F_5$,5.7), 117($C_5F_3$,0.6), 105($C_4F_3$, 0.4), 100($C_3F_4$,1.7), 93($C_3F_3$,1.6), 74($C_3F_2$,1.0), 69($CF_3$, 100), 50($CF_2$,1.3).

Example 6

Direct Fluorination of Perfluoro(2,4-dimethyl-3-isopropyl-2-pentene) (0° C.)

Perfluoro(2,4-dimethyl-3-isopropyl-2-pentene) (3.1 g, 6.2 mmol) obtained in Example 3 was placed in a 10-ml fluororesin-made reaction tube, and dissolved in 5 ml of FC-72. A fluororesin-made magnetic stirrer was placed, then a fluorine gas inlet tube was placed at the bottom of the test tube, and the reaction container was cooled in ice-water bath. A pure fluorine gas was introduced and the mixture was stirred vigorously. After reaction for 30 days, the starting material was entirely converted into perfluoro(2,4-dimethyl-3-isopropyl-3-pentyl). Gas chromatography revealed that the reaction proceeded quantitatively. The structure was identified by ESR as similar to Example 1.

Example 7

Direct Fluorination of Perfluoro(2,4,4-trimethyl-3-isopropyl-2-pentene) (0° C.)

Perfluoro(2,4,4-trimethyl-3-isopropyl-2-pentene) (80 mg, 0.145 mmol) obtained in Example 4 was placed in a 10-ml fluororesin-made reaction tube and dissolved in 5 ml of FC-72. A fluororesin-made magnetic stirrer was placed, then a fluorine gas inlet tube was placed at the bottom of the test tube, and the reaction container was cooled in ice-water bath. A pure fluorine gas was introduced and the mixture was stirred vigorously for 4 hours. The gas chromatography analysis of the reaction solution revealed that 30.7% by weight of the raw material was consumed and converted into perfluoro(2,4-dimethyl-3-isopropyl-3-pentyl) which is a super-stable perfluoroalkyl radical and perfluoro(2,4-dimethyl-3-isopropyl-2-pentene). The yields based on the consumed raw material were 35.2% by weight and 64.8% by weight, respectively.

What is claimed is:

1. A highly branched perfluoroolefin represented by the following general formula (1):

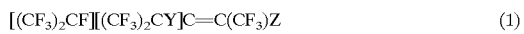  (1)

in the formula, Y and Z are the same or different, Y represents Rf, Z represents F or Rf, and Rf represents a straight or branched perfluoroalkyl group having 1 to 16 carbon atoms, provided that Y and Z are not simultaneously F.

2. The highly branched perfluoroolefin according to claim 1,
which is perfluoro(2,4,4-trimethyl-3-isopropyl-2-pentene) or perfluoro(4,4-dimethyl-3-isopropyl-2-pentene).

* * * * *